United States Patent
Fiechter et al.

(10) Patent No.: US 10,335,203 B2
(45) Date of Patent: Jul. 2, 2019

(54) POLYAXIAL SCREW FOR SURGICAL IMPLANT

(71) Applicant: MEDACTA INTERNATIONAL SA, Castel San Pietro (CH)

(72) Inventors: Meinrad Fiechter, Lugano (CH); Marco Magni, Uggiate-Trevano (IT); Daniele Beretta, Maslianico (IT); Francesco Siccardi, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 0 days.

(21) Appl. No.: 15/328,679

(22) PCT Filed: Jun. 25, 2015

(86) PCT No.: PCT/IB2015/054785
§ 371 (c)(1),
(2) Date: Jan. 24, 2017

(87) PCT Pub. No.: WO2016/016745
PCT Pub. Date: Feb. 4, 2016

(65) Prior Publication Data
US 2017/0209184 A1 Jul. 27, 2017

(30) Foreign Application Priority Data

Jul. 30, 2014 (IT) .............................. MI2014A1383

(51) Int. Cl.
*A61B 17/70* (2006.01)
*A61B 17/86* (2006.01)
*A61B 17/00* (2006.01)

(52) U.S. Cl.
CPC ...... *A61B 17/7037* (2013.01); *A61B 17/7032* (2013.01); *A61B 17/8665* (2013.01); *A61B 2017/00862* (2013.01)

(58) Field of Classification Search
CPC .................. A61B 17/70; A61B 17/7035–7046
See application file for complete search history.

(56) References Cited

U.S. PATENT DOCUMENTS

| 8,075,603 B2 | 12/2011 | Hammill, Sr. |
| 2004/0267264 A1* | 12/2004 | Konieczynski .... A61B 17/7032 606/289 |

(Continued)

FOREIGN PATENT DOCUMENTS

| EP | 2502594 | 9/2012 |
| JP | 2007526007 | 9/2007 |

(Continued)

*Primary Examiner* — Eduardo C Robert
*Assistant Examiner* — Michelle C Eckman
(74) *Attorney, Agent, or Firm* — Allen, Dyer, Doppelt + Gilchrist, P.A.

(57) ABSTRACT

A polyaxial screw for surgical implant comprising an axially hollow central body; an anchoring element having an anchoring portion and a coupling portion, said anchoring portion projecting from said central body and said coupling portion being received inside the axial cavity of said central body; an insert axially received inside said axial cavity of the central body and an attachment element suitable to couple internally to said central body, characterized in that said insert has an elastic portion able to apply to at least a portion of the anchoring element a distributed compression load the resultant force of which being directed along the central axis X.

7 Claims, 8 Drawing Sheets

(56) References Cited

U.S. PATENT DOCUMENTS

| | | | |
|---|---|---|---|
| 2011/0152949 A1 | 6/2011 | Biedermann | |
| 2011/0282399 A1* | 11/2011 | Jackson | A61B 17/702 606/305 |
| 2012/0310284 A1* | 12/2012 | Gerchow | A61B 17/7037 606/264 |
| 2013/0131734 A1* | 5/2013 | Longtain | A61B 17/7037 606/305 |
| 2013/0150852 A1* | 6/2013 | Shluzas | A61B 17/7032 606/65 |
| 2013/0338721 A1* | 12/2013 | Biedermann | A61B 17/7037 606/305 |
| 2014/0321945 A1* | 10/2014 | Black | F16B 29/00 411/383 |
| 2015/0032162 A1* | 1/2015 | Biedermann | A61B 17/7032 606/278 |
| 2015/0196337 A1* | 7/2015 | Biedermann | A61B 17/7037 606/305 |
| 2015/0196338 A1* | 7/2015 | Biedermann | A61B 17/7037 606/305 |
| 2015/0282843 A1* | 10/2015 | Spitler | A61B 17/7037 606/266 |
| 2016/0262803 A1* | 9/2016 | Nelson | A61B 17/7037 |

FOREIGN PATENT DOCUMENTS

| | | |
|---|---|---|
| JP | 2011500279 | 1/2011 |
| JP | 2012196453 | 10/2012 |
| JP | 2014507970 | 4/2014 |
| WO | 2010065648 | 6/2010 |
| WO | 2015155658 | 4/2015 |

* cited by examiner

POLYAXIAL SCREW FOR SURGICAL IMPLANT

The present invention provides a polyaxial screw for surgical implantation.

In the state of the art a variety of systems and techniques are known to intervene on specific dysfunctions of the spine, such as abnormal curvature of the spine, injuries to the same, etc.

The intervention on these types of spine-specific problems frequently requires the stabilization of a portion of the spine portion so as to facilitate the fusion of two or more vertebrae together in a single bone agglomeration.

This type of intervention is frequently employed for the correction of many pathological conditions of the spine such as, for example, degenerative diseases of the discal elements, scoliosis, spinal stenosis, or the like.

The stabilization of the spine allows the creation of a bone tissue in the intervertebral part; in this way, a part of the spine is fused into a single bone body.

The stabilization of the spine has been studied for a long time in the past and a variety of methods and devices have been developed for the correction of many pathologies that affect characteristically this body part in order to stabilize the its configuration, facilitating the vertebral fusion at various levels.

One of these known systems provides that a corrective rod is arranged longitudinally along the portion of the spine, which needs the intervention. This corrective rod is shaped in such a way as to restore the correct anatomical shape, which is characteristic of that specific portion of a healthy spine.

With this method, therefore, the corrective rod is positioned along the spine to engage various vertebrae, as needed. It should be noted that, typically, in this type of surgery two parallel corrective rods are used that are arranged posterior to the sides of the central zone of the patient's spine. Therefore, during said surgery, the pair of corrective rods is fixed to the spine by means of various fixing means, including, for example, screws. These screws are attached to the bone structure, typically to the vertebral pedicle.

The inclination of the corrective rod and, consequently, the positioning of the attachment screws varies depending on the type of correction to be done and, of course, from vertebra to vertebra. One type of screws known in the state of the art, which are widely employed in said application, are the screws of the polyaxial type, in which the head of the screw can vary its angle to the threaded stem to better fit the surgical needs as long as it is not coupled to it a attachment screw. It seems clear that it is essential for a successful surgery to properly fix both the corrective rod and the screws to which the rod will be fixed. In fact, the corrective rod is inserted into a head of the polyaxial screw and secured to it by means of the attachment of a attachment screw, coupled by means of a helical coupling, in such a way that, after the coupling, said attachment screw is locked in the desired position and the corrective rod is fixed inside the housing provided in the screw head. Therefore, as long as the attachment screw is not correctly coupled, the head of the polyaxial screw is free to move.

An example of what has been briefly described is illustrated in numerous patent and scientific literature documents. For example, EP2502594A1 of the same applicant discloses a polyaxial screw comprising a receiving part extending longitudinally from a first proximal opening to a second distal opening; said receiving part also comprises a U-shaped transverse passage provided with side openings on the perimeter of said receiving part. A threaded stem passes through the proximal opening of said receiving part and extends exteriorly along the entire threaded portion, while a portion of a substantially spherical shape is rotatably housed within said receiving part. Above said spherical portion is located a locking insert, whose part in contact with the spherical portion is such as to fit the shape of said spherical portion and is adapted to be disposed in a locking position, in which it locks the relative movement between the threaded stem with its spherical portion and the receiving part. Above said insert is housed the corrective rod, received through the U-shaped transverse passage and locked in the upper position by an attachment screw. Said attachment screw engages an inside screw thread near the distal opening of the receiving part and, by means of its helical coupling with the said receiving part, moves axially up to urge against the corrective rod, the underlying locking insert and the spherical portion, to block in this way the possible relative movements between the component parts of the polyaxial screw. However, as it is known from the art, the rod must be accurately positioned at accurate corrective positions. For this, it is therefore necessary that the alignment between the plurality of polyaxial screws and, more precisely, between the plurality of receiving parts housing the corrective rod is as correct as possible depending on the geometry selected by the surgeon, in order to respect the anatomy of the patient.

To ensure an easier positioning of the corrective rod, in the above-mentioned EP2502594A1 by the same applicant it is known a polyaxial screw as described previously and characterized in that it has, along its receiving part, a side opening through which it is possible to operate in pressure on a contact surface of the locking insert so as to urge it against the underlying spherical portion to block it temporarily in position.

However, this operation requires that the surgeon use an appropriate instrument that has to be kept in position during the insertion operations of the rod in order to lock in position the receiving part. After the tool has been removed, the locking is released and the receiving part is again free to move relative to the threaded stem until the attachment screw is not coupled to the receiving part, as previously described.

Since the length of said corrective rod is such as to comprise a plurality of vertebrae, it is clear the need for a device that is able to maintain a predetermined preliminary configuration during the implantation without the intervention of the surgeon and/or external means.

A device like the one disclosed in the document U.S. Pat. No. 8,075,603 of Ortho Innovation LLC has been used to meet this need. Said document discusses a device substantially similar to that described previously in which, on the periphery with respect to the central axis of the receiving part, recesses are provided within which springs are positioned. Said springs are interposed between the receiving part and a locking insert below which a spherical portion is provided integrally connected with a threaded stem. The springs are in preload configuration, in such a way as to provide a constant pressure on said locking insert with a force such as not to allow the free relative movement of the spherical portion of the stem of the polyaxial screw with respect to the receiving part. The surgeon, by using a force such as to overcome the force applied by the springs, is able to perform a movement relative to the spherical portion of the stem of the polyaxial screw with respect to the receiving part, selecting in this way the correct positioning of said receiving part and then inserting the corrective rod in its seat.

However, even this solution has some drawbacks.

A drawback encountered in the state of the art is the positioning of the springs with respect to the central axis of the receiving part. In fact, as disclosed in U.S. Pat. No. 8,075,603, it is proposed as symmetrically eccentric with respect to the central axis of the receiving portion. However, during the implantation of the polyaxial screw, this eccentricity can result in a lack of homogeneity of the force exerted by the locking insert on the spherical portion, resulting in an operating difficulty during the implantation steps.

Furthermore, in order to increase the zone on which the eccentric force imparted by each of the two springs is applied, the device known in the art provides for an upper retaining element, on which two springs act, which is positioned above the spherical head of the threaded stem, and a lower retaining element placed below said spherical head. In this way, the two springs act in compression laterally on the retaining element to urge it against the spherical head of the threaded stem, which spherical head, in turn, is urged against the lower retaining element. This configuration, in addition to requiring a special precision machining processing on the upper retaining element, multiplies the number of elements involved in the transmission of lateral force exerted by the springs, resulting in an increased risk of malfunction, errors in the assembly of the device, wear, and poor reliability of the component.

Additionally, the said device disclosed in the document U.S. Pat. No. 8,075,603 provides that the spherical head of the stem of the screw is retained inside the central body by means of the lower retaining element. Said lower retaining element is coupled to the central body releasably so as to become detached and to allow the spherical head of the threaded stem to access its seat provided in operative conditions. The insertion of the spherical head then takes place from below. This configuration, therefore, further multiplies the number of elements needed for the realization of the device, thereby increasing the risk of malfunction, decreasing the safety of the device, and increasing the costs of realization, as well as the assembly and implantation times.

Additionally, the processing costs, the assembly time and the overall dimensions required by the inherent structural characteristics of the prior art are particularly severe drawbacks.

Based on the concept of such objects, the present invention intends to remedy it.

An object of this invention is to provide a polyaxial screw for surgical implantation, which makes easier its implantation by the user.

A further object of the present invention is to provide a polyaxial screw for surgical implantation whose locking insert comprises a direct axial load on the spherical portion of the threaded stem in order to temporarily lock it relative to the receiving part.

Another object of the present invention is to provide a polyaxial screw for surgical implant that is able to minimize the number of elements in order to increase safety, reduce malfunction causes, and reduce manufacturing costs and assembly times.

Still object of the present invention is to provide a polyaxial screw, as described, which is of simplified structure, easy implantation, low cost, and rapid assembly.

In view of these objects, the present invention provides a polyaxial screw for surgical implant, whose basic characteristic is the subject of claim 1.

Further advantageous features are listed in the dependent claims.

All claims are considered as described.

The present invention will be described in detail by way of example only with the aid of the accompanying drawings, in which.

Figure 1:
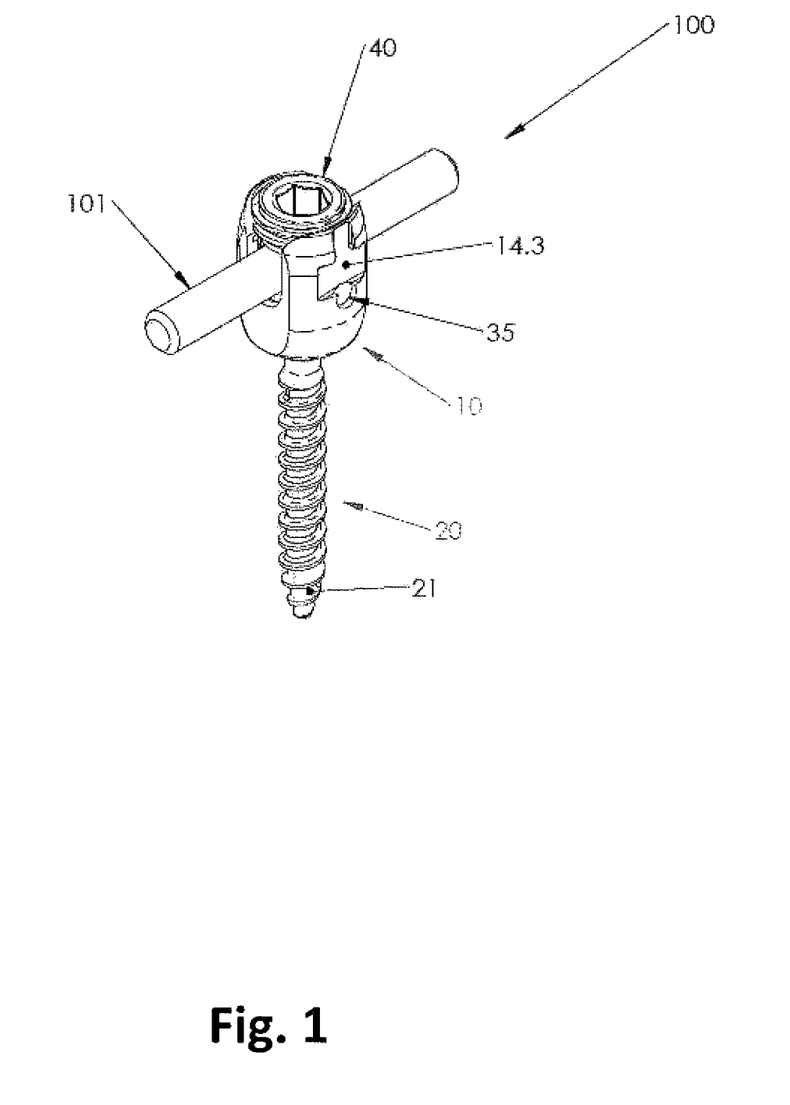
FIG. 1 is a front elevational view of a polyaxial screw for surgical implant according to the present invention when pre-assembled and coupled with a corrective rod.
Figure 2:
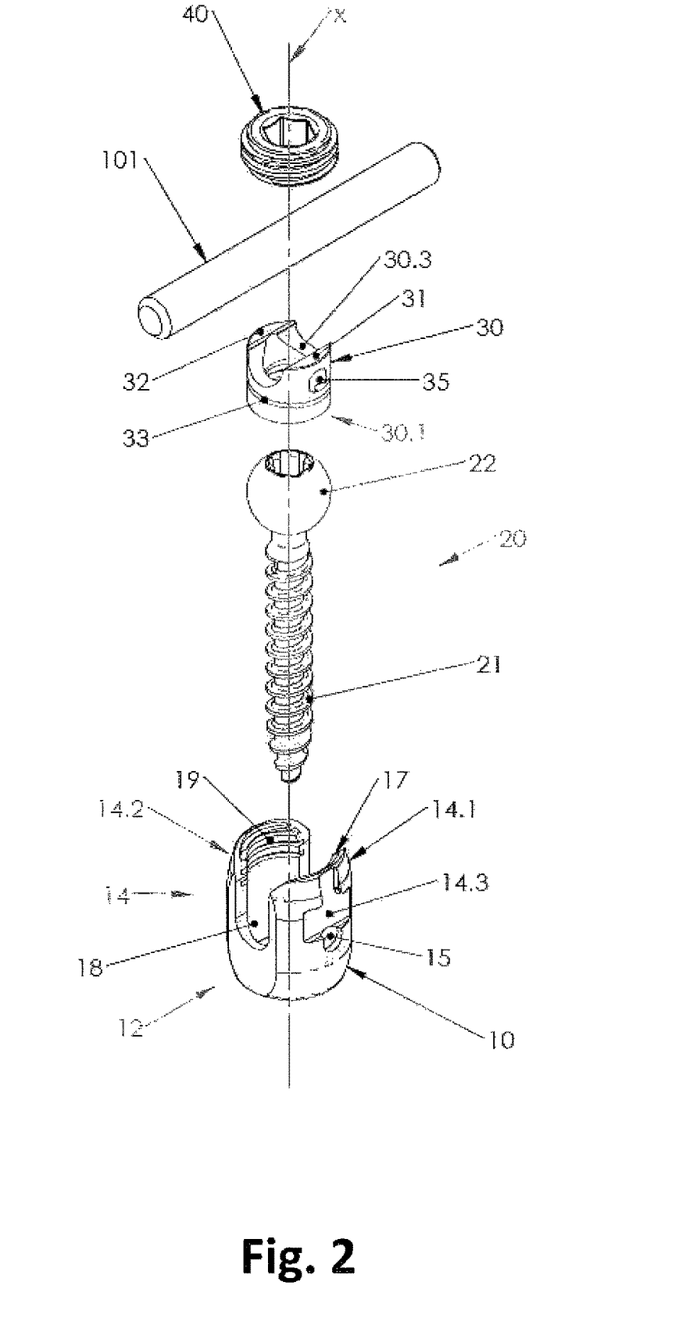
FIG. 2 is an exploded front elevational view of a polyaxial screw for surgical implant according to the present invention with a corrective rod.

In the drawing, 100 refers to a polyaxial screw for surgical implant according to the present invention. It includes (FIG. 2) a central body 10, preferably from a metal material, having a substantially frustoconical shape with a central axis X, with a through cylindrical axial cavity and has two zones: an upper zone 14 and a lower zone 12. In the upper zone 14 of the central body 10, there are two U-shaped through notches 17 and 18 and occupying the entire axial development of the upper zone 14 of the central body 10. Said notches 17 and 18 divide the said upper zone 14 of the central body 10 into two distinct portions 14.1 and 14.2. Said two portions 14.1 and 14.2 have a section in circular crown sectors, are symmetrical to each other, arranged frontally to one another, and each comprise a threaded free upper end with a nut thread 19 and a lower end forming one body with the lower zone 12. At said lower ends of the portions 14.1 and 14.2 there is a channel 50 (FIG. 6) having an axis transverse to the central axis of the central body 10 formed by the U-shaped jointed terminal part of the notches 17 and 18.

Figure 3:
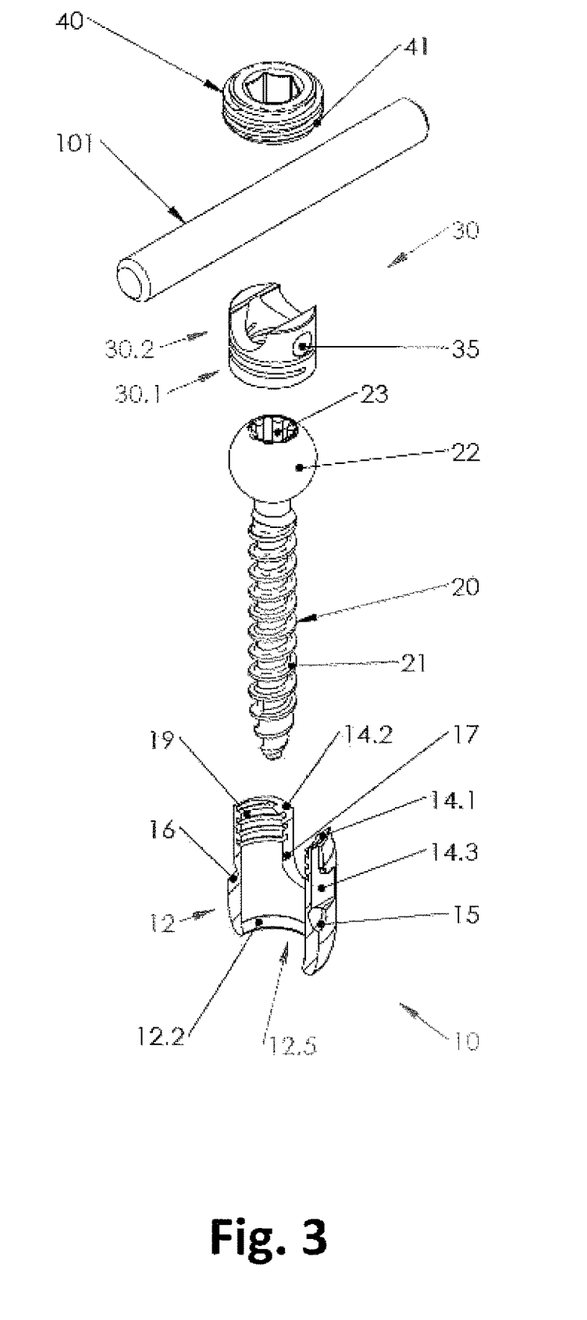
FIG. 3 is an exploded front elevational view and in partial cross-section of a polyaxial screw for surgical implant according to the present invention with a corrective rod in which the central body is sectioned along the line D-D of FIG. 8.

The lower zone 12 of the central body 10 has a substantially cylindrical shape and is open at the bottom (FIG. 3). Peripherally with respect to a lower opening 12.5 of the lower zone 12 of the central body 10, there is a stop portion, for example a lip 12.2, projecting towards the inside of the axial cavity.

Figure 6:
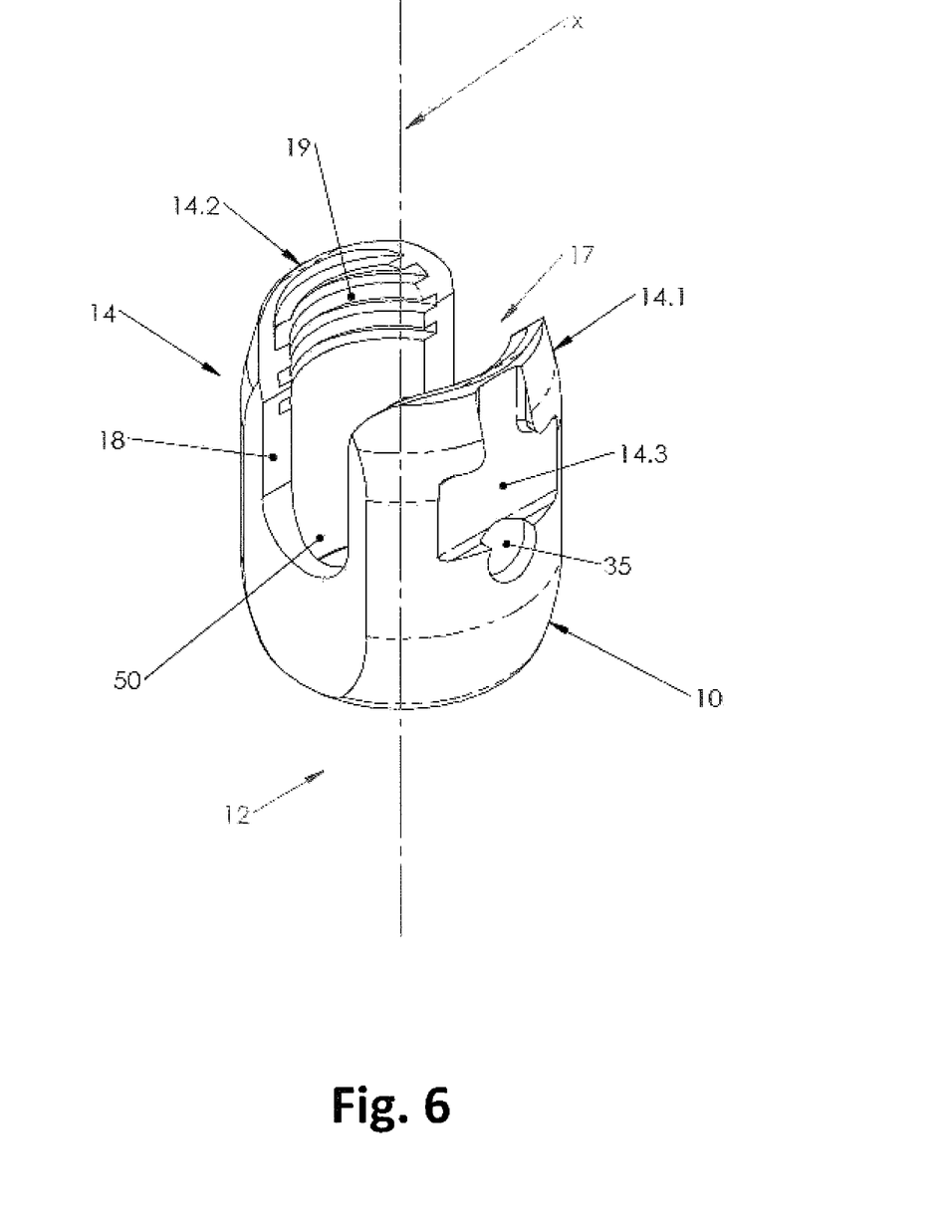
FIG. 6 is a ¾ view from above of the central body of the polyaxial screw for surgical implant according to the present invention.
Figure 7:
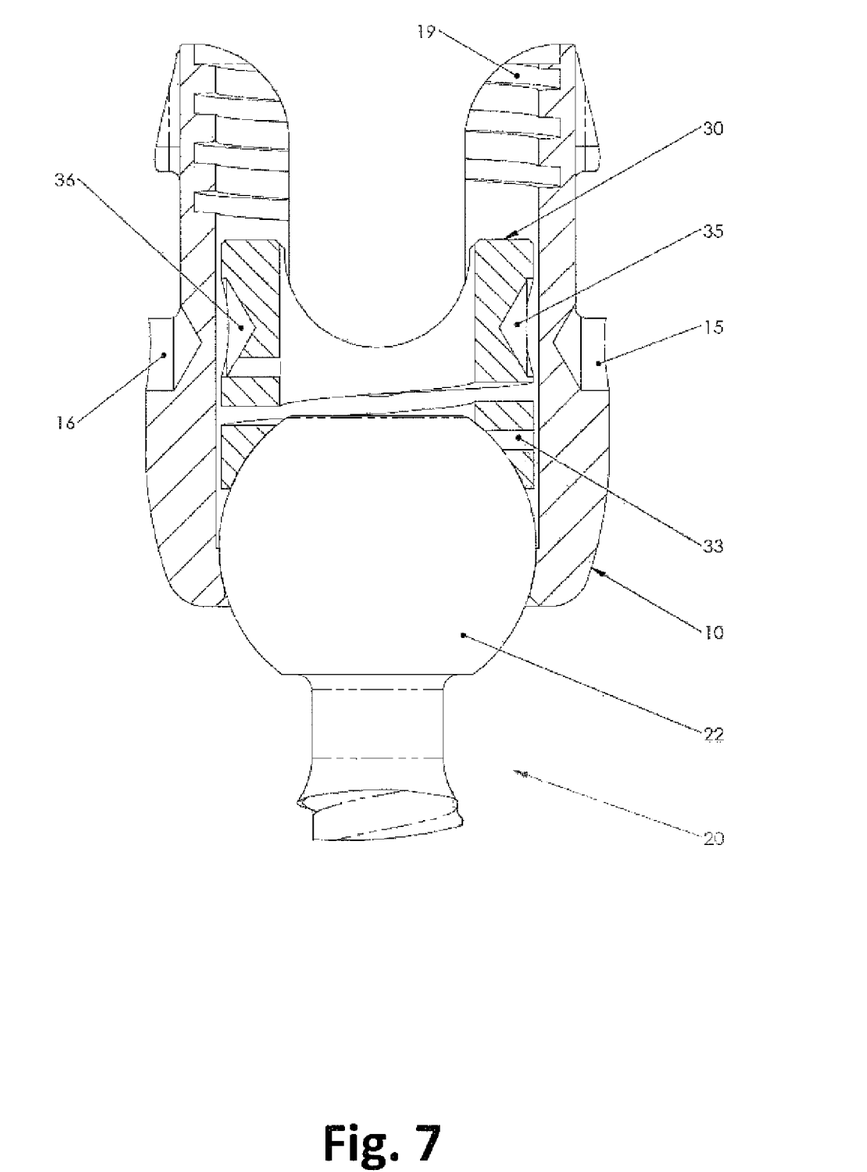
FIG. 7 is a sectional view along the line D-D of FIG. 8 of the polyaxial screw for surgical implant according to the present invention during a pre-assembly phase.
Figure 8:
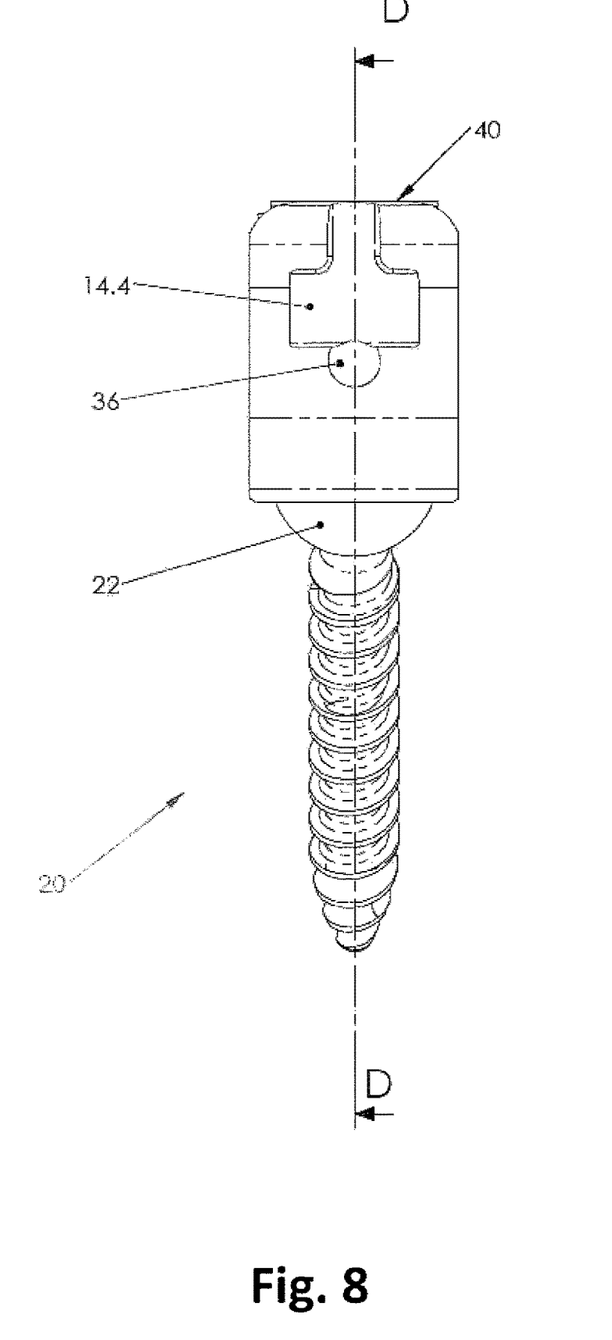
FIG. 8 is a side elevational view of the polyaxial screw for surgical implantation in a pre-assembled configuration.

On the outer surface of the central body 10 there are two receiving zones, for example two non-through grooves 14.3 and 14.4 (FIG. 6). Said grooves 14.3 and 14.4 have the form of an inverted "T" and extend for the entire vertical development of the portions 14.1 and 14.2, and are adapted to receive, during the implantation, respective centering prongs of a screwdriver, for example the instrument disclosed in the document MI2014A000649 of the same Applicant, for the coupling of a attachment screw 40 with the central body 10.

At the base of the grooves 14.3 and 14.4, near the lower zone 12 of the central body 10, there are two holes, respectively a hole 15 at the base of the groove 14.3 and a hole 16 at the base of the groove 14.4 (FIG. 3). In one embodiment, for example the embodiment illustrated only by way of non limiting example in the attached drawings, the said holes 15 and 16 are blind; however, it may be expected that said holes 15 and 16 are through holes, without departing from the scope of the present invention.

In addition, the polyaxial screw 100 has an anchoring element 20, preferably made from a metal material, which comprises an anchoring portion, for example a threaded stem 21, located in the proximal position and a coupling portion, for example a spherical head 22, positioned in the distal position. Said threaded stem 21 and said spherical head 22 are integrally connected to each other, preferably made in a single body, for example from a metal material. It should be noted that on the free end of the spherical head 22 there are known actuating means 23 for the implantation of the anchoring element 20. The threaded stem 21 and the spherical head 22 of the anchoring element 20 have such dimensions as to be able to be inserted axially within the axial cavity of the body 10, by inserting said anchoring element 20 from the side of the threaded stem 21 through and making it move to the entire axial length of the central body 10 (i.e. in the proximal-distal orientation), so that said threaded stem 21 is fully extended out from the lower opening 12.5 provided in the lower zone 12 of the central body 10, while the spherical head 22 comes into abutment on the lip 12.2 provided inside the lower opening 12.5, so as to be retained for substantial part of its axial development within the axial cavity of the central body 10.

Figure 4:
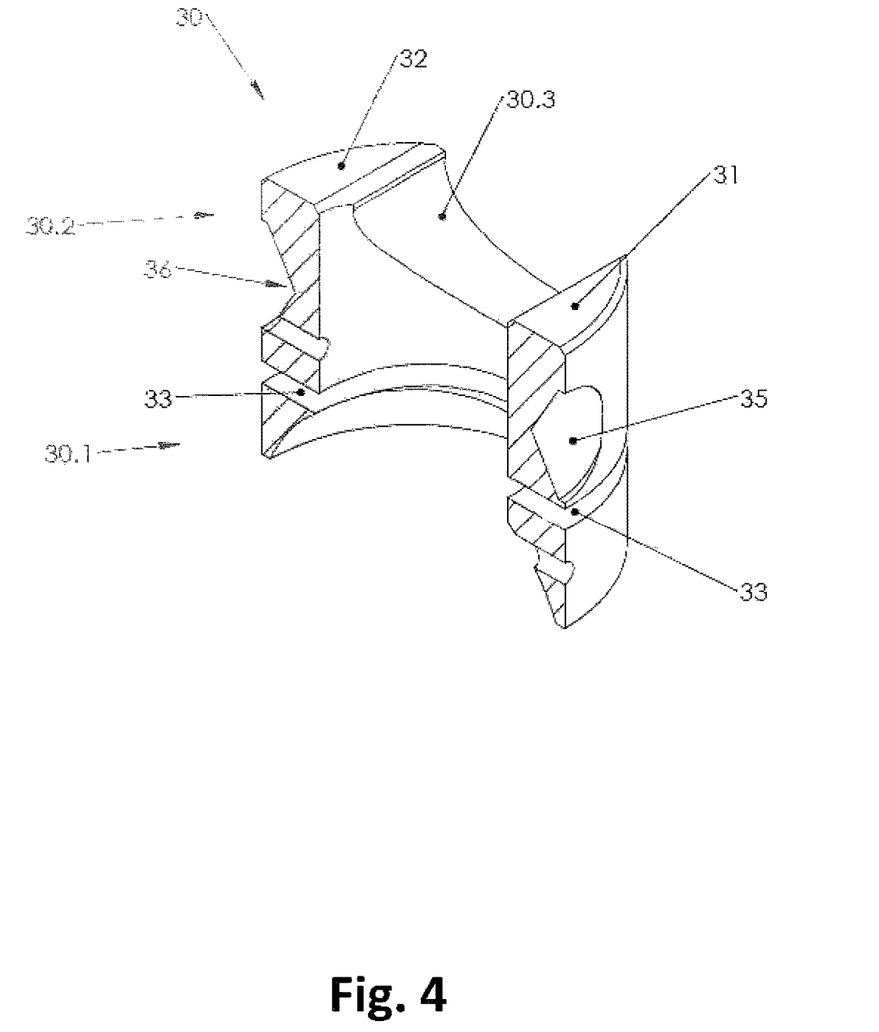
FIG. 4 is a front elevational view at an enlarged scale in cross-section of an insert of the polyaxial screw for surgical implant according to the present invention along the line D-D of FIG. 8.
Figure 5A:
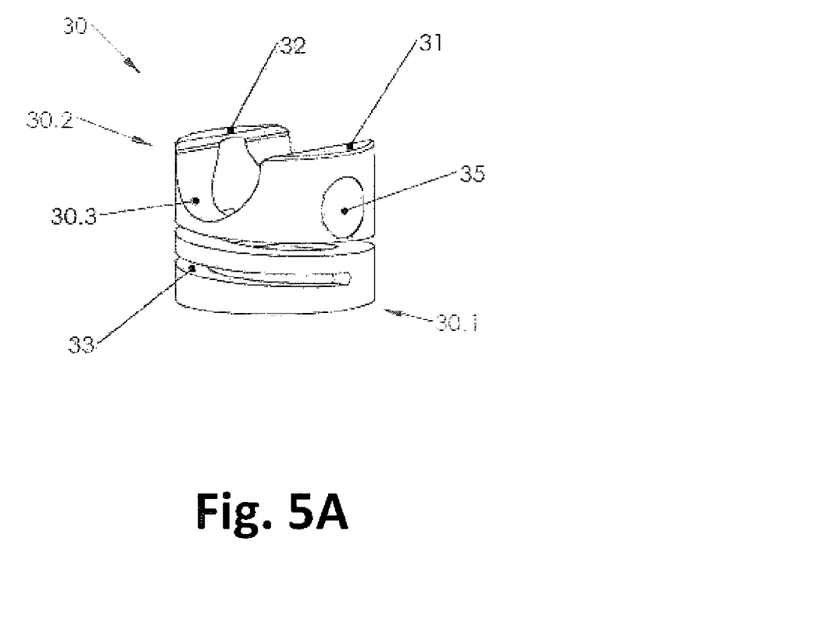
FIG. 5A is a front elevational view of the insert of the polyaxial screw for surgical implantation.
Figure 5B:
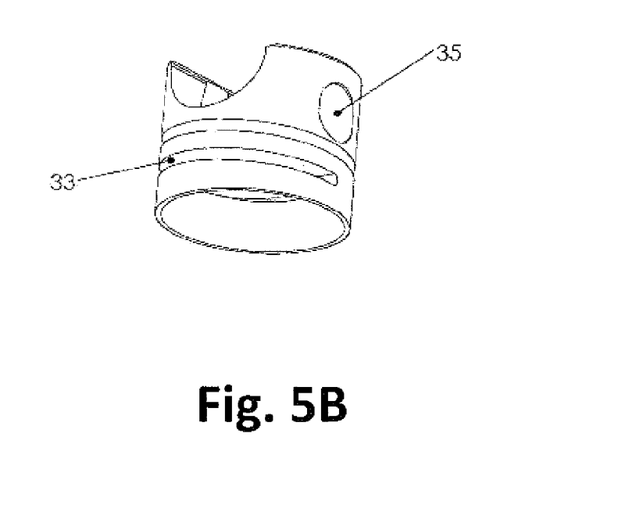
FIG. 5B is a ¾ view from below of the insert of the polyaxial screw for surgical implant according to the present invention.

The polyaxial screw 100 has also an insert 30. Said insert 30 is preferably made from metal material and has dimensions such as to be received inside the axial cavity of the central body 10, and has two parts (FIG. 4): a first proximal portion, said elastic portion 30.1 and a second distal portion 30.2. The insert 30 has a cylindrical shape, with an inner axial cavity at its elastic portion 30.1 and has two perimetric protrusions 31 and 32 at its distal portion 30.2. Said two protrusions 31 and 32 are connected to the elastic portion 30.1 of the insert 30 in such a way as to form a saddle zone 30.3 with it. That saddle zone 30.3 has a semi-cylindrical conformation and is placed at the joining zone between the distal portion 30.2 and the elastic portion 30.1 of the insert 30. On the outer surface of the distal portion 30.2 of the insert 30 there are two receiving elements, for example the blind holes 35 and 36. Below said blind holes 35 and 36, at the elastic portion 30.1 and for substantial part thereof, there is a perimetral groove 33. Said groove 33 has a helical conformation and departs from the periphery of the lower edge of the elastic portion 30.1, possibly engaging it, to arrive near the distal portion 30.2. The helical conformation of the perimetral groove 33 and the elastic properties typical of the material of the insert 30 and/or part of it, for example the elastic portion 30.1, cause that said groove 33 to impose to the elastic portion 30.1 a behaviour of an elastic means, when the insert 30 is subjected to a compressive axial force, for example a distributed compression load.

Of course, it is clear to the skilled in the art that the shape, the position and number of the grooves 33 can be varied without departing from the scope of protection of the present patent. For example, the groove 33 could be replaced by a plurality of grooves, notches or openings of any shape such as to give elasticity to the elastic portion 30.1. Likewise, it is clear to the skilled in the art that the choice of a material with certain characteristics capable of transmitting an axial compressive force, for example a distributed compression load, as described above, without using one or more grooves 33, cannot be regarded as outside the scope of protection of the present invention.

Finally, the polyaxial screw 100 has a fixing element, for example a attachment screw 40, having perimetral thread 41 adapted to be coupled to the nut thread 19 at the portions 14.1 and 14.2. On the top of the attachment screw 40 there are engagement means for engage said attachment screw 40 with tools for its implantation, such as for example screwdrivers, hex keys or other tools known in the art.

Method of Pre-Assembly

The method of pre-assembly of the polyaxial screw 100 according to the present invention comprises the following phases:

A first phase of insertion, wherein the anchoring element 20 is inserted axially inside the axial cavity of the central body 10 by means of translation, up to bring the coupling portion, for example the spherical head 22, in abutment against a stop portion, for example the lip 12.2 of the central body 10, so that the anchoring portion, for example the threaded stem 21, protrudes for the entire length thereof outside of the central body 10; said insertion takes place in a proximal-distal orientation with respect to the anchoring element 20, i.e. the said anchoring element 20 is inserted inside the axial cavity of the central body 10 "from above".

A second phase of insertion, wherein the insert 30 is inserted axially, by means of translation, inside the axial cavity of the central body 10, up to bring the elastic portion 30.1 against at least an upper part of the spherical head 22 of the anchoring element 20, taking care to align, on the same orientation line, the blind holes 35 and 36 with the holes 15 and 16 of central body 10, respectively.

A preload phase during which, possibly by means of a special tool (not shown), for example a presser, an preload axial force is applied, i.e. a distributed compression load, in order to axially press the insert 30 against the spherical head 22 of the anchoring element 20. The presence of the groove 30 and/or the inherent elasticity of the component material of the insert 30 allow an elastic deformation of the proximal part 30.1 of said insert 30, in such a way that the holes 35 and 36 are centered with respect to the holes 15 and 16 provided at the outer surface of the central body 10. By this operation, the channel 50 is also aligned to the saddle zone 30.3 of the insert 30.

A locking step during which, while maintaining the previously-imposed preload, i.e. the imposed distributed compression load, by means of a deflecting device, for example a punch, the bottom wall 15.1 and 16.1 of the holes 15 and 16, respectively, provided in the central body 10, is deformed, forcing said bottom walls 15.1 and 16.1 to protrude inside the holes 35 and 36, respectively. In this manner, the bottom walls 15.1 and 16.1 of the holes 15:16 act as locking means. In this way, the insert 30 is constrained to the central body 10 in preload conditions; this allows the elastic portion 30.1 of said insert 30 to act in pressure on the spherical head 22 of the anchoring element 20, preventing it to rotate freely with respect to the central body 10. After the locking phase, the preload axial force can be removed.

A third phase of insertion, by which an attachment element is inserted, for example the attachment screw 40, by means of a special tool, At the end of said method, the polyaxial screw 100 according to the present invention is in pre-assembled conditions, ready for implantation.

It should be noted that, as will be clear to the person skilled in the art, the anchoring element 20 is not able to rotate freely with respect to the central body 10 because of the locking force imposed by the insert 30 fixed in preload conditions, as stated above. This locking force is manifested, on top, as a friction between at least a part of the coupling portion, i.e. the spherical head 22, and the elastic portion 30.1 of the insert 30, while, from the below, as a friction between said coupling portion, i.e. the spherical head 22, with at least a part of the lower zone 12 of the central body 10.

However, if it is necessary to give a desired angle to the anchoring element 20 with respect to the main body 10, for the correct implantation of the polyaxial screw 100, it will be enough to apply to the central body 10 (alternatively to the threaded stem 21 of the anchoring element 20) a small force able to overcome the locking force imposed by the spring portion 30.1 of the insert 30. In this manner, the anchoring element 20 will attain the desired angle, which will be kept constant thanks to the locking action applied by the elastic portion 30.1 of said insert 30, until a new change is set by the user.

Implantation

The polyaxial screw 100 according to the present invention is used, in particular, during minimally invasive surgery of the spine. In these cases, the surgeon, after having decoupled the attachment screw 40 from the central body 10, performs the attachment of the anchoring element 20 within a part of the vertebra called "pedicle". Said attachment is carried out, for example, by coupling the threaded stem 21 of the anchoring element 20 to the pedicle (not shown in the drawings). After inserting the threaded stem 21 within the pedicle, the surgeon chooses the correct angle of the main body 10 with respect to the threaded stem 21, said correct angle varying depending on the geometry required by the surgical implant. Therefore, once said correct angle is identified, the central body 10 is not free to independently vary its angle with respect to the anchoring element 20, thanks to the aforementioned locking force exerted by the elastic portion 30.1 of the insert 30; in this manner, the surgeon performs the insertion of a corrective rod 101 within the channel 50, formed by the saddle zone 30.3 and by the U-shaped notches "U" 17 and 18.

On the completion of the insertion of the corrective rod 101 within the channel 50 of the central body 10, the surgeon performs the reinsertion of the attachment screw 40 in its threaded seat, comprised between the portions 14.1 and 14.2 of the central body 10, and the coupling thereof by threaded coupling.

The coupling of the attachment screw 40 to the central body 10 is performed, as mentioned, by means of tools known in the art, for example screwdrivers, or the like. However, in order to obtain a perfect axial alignment between the attachment screw 40 and the central body 10, the state of the art provides devices dedicated to the insertion and the coupling of said attachment screw 40 to the central body 10. An example of this known tool is the screwdriver described in the document number MI2014A000649 of the same Applicant, to which express reference is made herein for a detailed description of the tool. Said screwdriver has centering means adapted to engage the receiving zones 14.3 and 14.4 on the outer surface of the central body 10. These receiving zones 14.3 and 14.4 allow, therefore, a perfect centering of said known tool from the X axis of the said central body 10, allowing an optimum coupling of said attachment screw 40 to the central body 10, avoiding jamming phenomena, damages to the threads, and mating problems.

The attachment screw 40, during its coupling with the thread 19 on the top of the inner part of the portions 14.1 and 14.2 of the central body 10, drops axially within the axial cavity, while pressing against the corrective rod 101 during its descent.

Under the action of the pressure exerted by the attachment screw 40, the rod is forced to urge against the insert 30. Such pressure, exerted by the corrective rod 101 on the saddle zone 30.3 at the distal portion 30.2 of the insert 30, where it is received, is transmitted from the saddle zone 30.3 to the elastic portion 30.1 of the insert 30, and then transmitted to the spherical head 22 of the anchoring element 20 in the form of a distributed compression load. Therefore, the resultant force of said distributed compression load is manifested by a compressive force directed axially along the axis X of the central body 10. In this way, the spherical head 22 of the anchoring element 20 is permanently locked inside the central body 10, thereby fixing the polyaxial screw 100 in the correct position desired by the surgeon.

Advantages

As appears clearly from the above description, the present invention provides a polyaxial screw with locking insert able to achieve the objects listed above.

Particularly advantageous is the simplified structure of the polyaxial screw with locking insert 30, thanks to which it is possible to eliminate the use of elastic means in perimetral position compared to the central body, as taught in the prior art. The innovative solution proposed by the present invention, in fact, eliminates all the possible eccentricity of application of the locking force due to an incorrect positioning of the elastic means in the devices known in the prior art, which are defects that may make it difficult to use the known devices due to jamming phenomena and/or uneven distribution of the locking force. Furthermore, the reduction in the number of components allows greater reliability of the polyaxial screw according to the present invention.

Still an advantage of the present invention compared to the state of the art, is the provision a pressure force for the locking of the spherical head 22 that acts in the axial orientation with respect to the spherical head 22, regardless of the precision of the mechanical machining required for the positioning of the elastic means, and regardless of any differences in preload imposed on the elastic means.

Finally, the polyaxial screw of the present invention allows to reduce the dimensions, which is a feature of particular importance in minimally invasive surgery, and to lower costs thanks to a simplified structure and to a remarkable simplicity and speed of assembly.

Of course, numerous variations may be made in practice with respect to those described and illustrated by way of non-limiting example, without thereby departing from the scope of the present invention and, therefore, from the domain of the present industrial property right.

The invention claimed is:

1. A polyaxial screw for surgical implant comprising:
   an axially hollow central body having an outer surface and a top perimetral edge;
   an anchoring element having an anchoring portion and a coupling portion, said anchoring portion projecting from said central body and said coupling portion being received inside the axial cavity of said central body;

an insert axially received inside said axial cavity of the central body and an attachment element suitable to couple internally to said central body; and two diametrically opposed grooves along the outer surface of said central body extending from the top perimetral edge and configured to receive centering prongs of a surgical instrument;

wherein said insert has an elastic portion able to apply to at least a portion of the anchoring element a distributed compression load the resultant force of which being directed along a central axis X of the central body, the elastic portion of the insert has, on at least a part thereof, at least one groove having a helical development.

2. The polyaxial screw for surgical implant according to claim 1, wherein said distributed compression load generates a friction between at least a part of the coupling portion of the anchoring element and at least a part of the elastic portion of the insert on one side and between at least a part of said coupling portion and at least a part of the central body.

3. The polyaxial screw for surgical implant according to claim 1, wherein the central body has, on its outer surface, one or more receiving zones for the centered coupling of the attachment element with said central body.

4. A method of pre-assembly of a polyaxial screw for surgical implant comprising the steps of:

inserting an anchoring element inside a central body by translation in an axial direction and distal-proximal orientation, the central body having two diametrically opposed grooves along an outer surface extending from a top perimetral edge and configured to receive centering prongs of a surgical instrument;

inserting an insert inside the central body by axial translation, juxtaposing said insert upward in relation to a coupling portion of the anchoring element, in such a way that an elastic portion of the insert, which presents, on at least a part thereof, at least one groove having a helical development, comes into contact with at least part of said coupling portion;

imposing an axial pre-load force applied along an X axis of the central body on the insert and coupling said insert with the central body by plastic deformation of a locking means and forcing of said locking means to couple with respective receiving elements; and removing the axial pre-load force applied along the X axis on the insert.

5. The method of pre-assembly of a polyaxial screw for surgical implant according to claim 4, wherein the plastic deformation of the locking means takes place by punching.

6. A polyaxial screw for surgical implant comprising:

an axially hollow central body having an outer surface and a top perimetral edge;

an anchoring element having an anchoring portion and a coupling portion, said anchoring portion projecting from said central body and said coupling portion being received inside the axial cavity of said central body;

an insert axially received inside said axial cavity of the central body and an attachment element suitable to couple internally to said central body; and two diametrically opposed grooves along the outer surface of said central body extending from the top perimetral edge and configured to receive centering prongs of a surgical instrument;

wherein said insert has an elastic portion able to apply to at least a portion of the anchoring element a distributed compression load the resultant force of which being directed along a central axis X of the central body, the elastic portion of the insert has, on at least a part thereof, at least one closed groove having a helical development.

7. A polyaxial screw for surgical implant comprising:

an axially hollow central body having an outer surface and a top perimetral edge, two inverted T-shaped grooves extending from the top perimetral edge and configured to receive centering prongs of a surgical instrument, and a blind hole at a base of each of said inverted T-shaped grooves, each blind hole having a bottom wall;

an anchoring element having an anchoring portion and a coupling portion, said anchoring portion projecting from said central body and said coupling portion being received inside the axial cavity of said central body; and an insert axially received inside said axial cavity of the central body, the insert having two opposing holes on an outer surface thereof;

wherein said insert has an elastic portion able to apply to at least a portion of the anchoring element a distributed compression load the resultant force of which being directed along a central axis X;

wherein the bottom wall of each of said blind holes being deformed to protrude inside a respective opposing hole of the insert to lock said insert to said central body.

* * * * *